United States Patent [19]
Ryan et al.

[11] Patent Number: 5,614,414
[45] Date of Patent: Mar. 25, 1997

[54] LIQUID LIPOPROTEIN CONTROL

[75] Inventors: Wayne L. Ryan; Bradford A. Hunsley, both of Omaha, Nebr.

[73] Assignee: Streck Laboratories, Inc., Omaha, Nebr.

[21] Appl. No.: 413,477

[22] Filed: Mar. 30, 1995

[51] Int. Cl.$^6$ ........................................ G01N 31/00
[52] U.S. Cl. ........................ 436/13; 436/71; 424/520
[58] Field of Search ........................ 436/13, 8, 14–16, 436/71, 63; 424/520

[56] References Cited

U.S. PATENT DOCUMENTS

| | | | |
|---|---|---|---|
| 3,260,648 | 7/1966 | Fox | 167/84 |
| 3,751,381 | 8/1973 | Megraw | 33/16 |
| 3,853,465 | 12/1974 | Rush et al. | 23/230 |
| 3,891,573 | 6/1975 | Stary et al. | 436/13 |
| 3,955,925 | 5/1976 | Proksch et al. | 23/230 |
| 4,011,045 | 3/1977 | Bonderman | 436/13 |

(List continued on next page.)

FOREIGN PATENT DOCUMENTS

| | | |
|---|---|---|
| 1184836 | 4/1985 | Canada . |
| 106160 | 8/1986 | Japan . |

OTHER PUBLICATIONS

M. Burnstein et al., Lipoprotein–Polanion–Metal Interactions pp. 67–108.

Hirst, C.F., et al. "The cause of turbidity in lyophilised plasmas and its effects on coagulation tests J. Clin, Pathol.", 45:701–703 (1992).

Kroll, et al. "Nonlinearity of High–Density Lipoportein Cholesterol Determinations Is Matrix Dependent" Clinical Chemistry vol. 4, No. 3 pp. 389–394 (1994).

Kuzuya, et al. "Lipid peroxide and transition metals are required for the toxicity of oxidized low denisity lipoprotein to cultured endothelial cells" Biochimica et Biophysica Acta pp. 155–161 (1991).

Naito, et al. "Matrix Effects on Proficiency Testing Materials", Arch Pathol Lab Med. vol. 117, pp. 345–351 (Apr. 1993).

"Proficiency Testing, Matrix Effects, and Method Evaluation", Editorial, Clin. Chem. vol. 40, No. 3, pp. 345–346 (1994).

Rumsey, et al., "Cryopreservation with sucrose maintains normal physical and biological properties of human plasma low density lipoproteins", Journal of Lipid Research, vol. 33 (1992).

Warnick, et al., "The Measurement of Lipid and Lipoprotein Risk Factors: In Pursuit of Accuracy", Clin. Chem., vol. 28, No. 6, (1982).

Wieland et al., "Improved Assessment of Plasma Lipoprotein Patterns: IV. Simple Preparation of a Lyophilized Control Serum Containing Intact Human Plasma Lipoproteins", Clin. Chem., pp. 1335–1337, vol. 28, No. 6, (1982).

Product Information and Data Sheet for Quantimetrix I IDL PLUS™ CONTROL supplied from Quantimetrix Corp. Hawthorne, California (Mar. 1994).

Product Information and Data Sheet for Quantimetrix Serum Lipid Control supplied from Quantimetrix Corp. Hawthorne, California (Aug. 1994).

Product Information and Data Sheet for CIBA–CORNING MULTIQUAL® ASY I, II, III, Supplied from Ciba Corning Diagnostics Corporation, Irvine, California, (Oct. 31, 1994).

*Primary Examiner*—Carol A. Spiegel
*Assistant Examiner*—Rachel Freed
*Attorney, Agent, or Firm*—Harness, Dickey & Pierce, P.L.C.

[57] ABSTRACT

An accurate, stable, liquid lipoprotein control composition is provided. The control composition of the present invention preferably comprises lipoprotein, suffactant and a divalent cation. The control may further comprise a chelating agent. It has been surprisingly found that when suffactant and a divalent cation are added to lipoprotein, it performs like native lipoprotein in human serum, i.e., not aggregated or subject to matrix effects. In addition, the control composition of the present invention is stable for up to about 5 months at room temperature (about 22° C.) and up to about 12 months when refrigerated (about 2° C. to about 10° C.). Methods of making and using the control composition are also provided.

15 Claims, 6 Drawing Sheets

U.S. PATENT DOCUMENTS

| | | | |
|---|---|---|---|
| 4,045,176 | 8/1977 | Proksch et al. | 23/230 |
| 4,110,077 | 8/1978 | Klein et al. | 23/230 |
| 4,127,502 | 11/1978 | Li Mutti et al. | 252/408 |
| 4,188,188 | 2/1980 | Willner et al. | 23/230 |
| 4,189,400 | 2/1980 | Proksch et al. | 252/408 |
| 4,210,557 | 7/1980 | Handschuh | 252/408 |
| 4,216,117 | 8/1980 | Proksch et al. | 252/408 |
| 4,224,229 | 9/1980 | Proksch et al. | 260/397.2 |
| 4,226,713 | 10/1980 | Goldberg | 23/230 |
| 4,289,649 | 9/1981 | Harders et al. | 436/13 |
| 4,290,774 | 9/1981 | Girgis et al. | 23/230 |
| 4,298,441 | 11/1981 | Seidel et al. | 204/180 |
| 4,414,326 | 11/1983 | Goldberg | 435/11 |
| 4,474,887 | 10/1984 | Maier et al. | 436/71 |
| 4,486,531 | 12/1984 | Ziegenhorn et al. | 435/19 |
| 4,503,146 | 3/1985 | Yun et al. | 435/19 |
| 4,521,519 | 6/1985 | Draeger et al. | 436/17 |
| 4,579,825 | 4/1986 | Siedel et al. | 436/175 |
| 4,608,347 | 8/1986 | Bernstam | 436/175 |
| 4,626,511 | 12/1986 | Artiss et al. | 436/8 |
| 4,701,417 | 10/1987 | Portenhauser et al. | 436/13 |
| 4,708,939 | 11/1987 | Siedel et al. | 436/13 |
| 4,816,411 | 3/1989 | Yun et al. | 436/13 |
| 4,994,375 | 2/1991 | Posner et al. | 435/17 |
| 5,118,613 | 6/1992 | McGowan | 435/11 |
| 5,258,315 | 11/1993 | Vormbrock | 436/174 |
| 5,310,679 | 5/1994 | Artiss et al. | 436/18 |
| 5,411,870 | 5/1995 | Law et al. | 435/11 |

LIQUID LIPOPROTEIN CONTROL

FIELD OF THE INVENTION

The present invention relates generally to lipoprotein controls and more particularly, to a stable, liquid, lipoprotein control composition, and methods of making and using the same.

BACKGROUND OF THE INVENTION

Lipoproteins are water soluble conjugated proteins. They are conjugated with lipids-substances such as cholesterol, triglycerides and phospholipids. Cholesterol, triglycerides and phospholipids are all insoluble in aqueous solutions. They are conjugated to proteins which make them soluble in serum.

The association of cholesterol and lipoproteins with arteriosclerosis has led to the frequent evaluation of cholesterol and lipoprotein in human serum. It is known that elevated total cholesterol and elevated low density lipoprotein (LDL) cholesterol levels may lead to poor cardiovascular health while elevated high density lipoprotein (HDL) cholesterol does not have a negative influence on cardiovascular health and may even improve the condition of cardiovascular health. Because of the association of cholesterol and lipoproteins with cardiovascular health and because it has been demonstrated that LDL cholesterol can be decreased and HDL cholesterol increased by diet, exercise and drugs, several clinical assays have been developed to measure lipoprotein, triglycerides and cholesterol.

A typical assay for lipid analysis often includes values for cholesterol, triglycerides, HDL cholesterol, LDL cholesterol, phospholipids, cholesterol esters, free fatty acids, apolipoprotein A1 and apolipoprotein B. In routine practice, LDL cholesterol is estimated using the Friedwald equation wherein LDL cholesterol is calculated by subtracting measured HDL cholesterol and estimated very low density lipoprotein (VLDL) cholesterol (approximated as one-fifth of the serum triglyceride) from total cholesterol. HDL cholesterol may be measured by various methods such as density separation using ultracentrifugation, electrophoresis or enzyme-linked methods employing cholesterol oxidase and photometric measurement. When the later method is employed, the VLDL. and LDL cholesterol is first precipitated from the serum with reagents such as heparin, dextran sulfate and magnesium ion or phosphotungstate. The HDL cholesterol remaining in the supernatant can then be measured.

Controls are used to objectively evaluate the accuracy and precision of lipoprotein testing procedures. Unfortunately, the freezing and lyophilization of lipoprotein controls leads to aggregation and turbidity of lipoprotein solutions. Another disadvantage in lipoprotein controls is reconstitution of lyophilized controls which can lead to inaccuracies due to volumetric measurements. Various approaches to improving lipid controls (triglycerides and total cholesterol) have thus been developed.

For example, in U.S. Pat. Nos. 4,816,411 and 4,503,146 (incorporated by reference), turbidity in biological fluid such as plasma or serum is reduced by adding a surfactant and cholesterol esterase or lipase, to degrade the lipoproteins. These patents describe photometric assays for cholesterol and triglycerides, wherein clear samples are essential. U.S. Pat. Nos. 4,626,511 and 5,310,679 (incorporated by reference), also disclose reduction of turbidity by the addition of a surfactant and lipolytic enzyme to degrade the lipoproteins.

In U.S. Pat. No. 4,011,045 (incorporated by reference), lipoproteins are precipitated from serum by the addition of divalent cations and dextran sulfate. The large lipoproteins are discarded and the short chain triglycerides are added back to the serum. The added triglycerides in serum are then emulsified by using the surfactant alkylphenoxypolyethoxyethanol. The serum is then lyophilized and reconstituted to produce a clear preparation.

Similarly, in U.S. Pat. No. 3,955,925 (incorporated by reference), a clear, lyophilized control product is prepared by precipitating lipoproteins from serum with dextran sulfate and divalent cations and adding back to the serum bovine high density lipoprotein which has been purified. Surfactant is also used to remove turbidity in U.S. Pat. Nos. 5,258,315, 4,579,825 and 4,708,939 (incorporated by reference), although no control product is disclosed. Similarly in U.S. Pat. No. 4,289,649 (incorporated by reference), nonionic and ionic detergent is used to remove turbidity in a control for triglycerides and total cholesterol.

In U.S. Pat. No. 4,127,502 (incorporated by reference), the addition of arabinose, sorbitol, sucrose or glucosamine was shown to reduce the turbidity of lyophilized serum and U.S. Pat. Nos. 4,298,441, 4,045,176 and 4,216,117 (incorporated by reference), disclose that lyophilized control serum which contains non-reducing sugars is stable.

The following U.S. Patents and journal article, which are incorporated by reference herein, relate generally to lipid preparations: U.S. Pat. No. 3,751,381, 3,853,465, 4,189,400, 4,290,774, 3,260,648, 4,414,326 and Hirst, C. F. et al., *J. Clin. Pathol.* 45:701–703 (1992).

None of the above patents describe stable lipoprotein controls; they are all used for cholesterol and triglyceride standards only. Several recent journal articles make it clear that there is no lipoprotein control which adequately behaves like human serum. In particular, Naito et al., *Arch. Pathol. Lab. Med.* 117:345–351 (1993), describes the "matrix effects" of known lipoprotein controls used in proficiency studies. Matrix is defined by the National Committee for Clinical Laboratory Standards, Document EP10-T, Vol. 9, No. 3, November, 1988, as "all properties other than the property to be measured, that can have an effect on a measured value," and matrix effects is defined as "an analytic bias due to the matrix of the processed specimen being measured, that is exclusive of calibration." Naito points out that the matrix problems associated with lipoprotein controls severely hamper interlaboratory accuracy, standardization efforts, and monitoring of laboratory performance. It is thus suggested that efforts be made to improve lipoprotein controls so they behave more like human serum.

Likewise, in Kroll, M. H. et al., *Clin. Chem.* 40:389–394 (1994), it was shown that there is a lack of linearity in high density lipoprotein measurements. Available commercial controls were not linear and it was suggested that the non-linearity is due to alteration of the lipoproteins during lyophilization. Rej. R., *Clin. Chem.* 40:345–346 (1994) also addresses the inadequacy of available lipoprotein controls and stresses the importance of developing adequate preparations for standardization of methods. The level of importance of this issue is further indicated by an Omnibus Solicitation of the National Institutes of Health, PHS 95-1 (Dec. 1, 1994 Application Receipt Date). The title of the solicitation is "Development of proficiency testing materials free of the matrix effects that compromise accurate measurement of total cholesterol, HDL cholesterol, and LDL cholesterol."

It would thus be desirable to provide an accurate, stable, lipoprotein control. It would further be desirable to provide an accurate, stable, liquid, lipoprotein control that is not lyophilized and reconstituted or frozen and thawed. It would also be desirable to provide an accurate, complete, chemistry control which includes all lipoproteins.

SUMMARY OF THE INVENTION

An accurate, stable, liquid lipoprotein control composition is provided. The control composition of the present invention preferably comprises lipoprotein, surfactant and a divalent cation. It has been surprisingly found that when surfactant and a divalent cation are added to lipoprotein, it behaves like native lipoprotein in human serum, i.e. not aggregated and not subject to matrix effects. The control of the present invention may thus provide all of the lipid parameters: HDL cholesterol, LDL cholesterol, phospholipids, cholesterol esters, free fatty acids, apolipoprotein A1 and apolipoprotein B. Surprisingly, the control composition of the present invention is stable for up to about 5 months at room temperature (about 22° C.) and up to about 12 months refrigerated (about 2° C. to about 10° C.). Methods of making and using the control composition are also provided.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
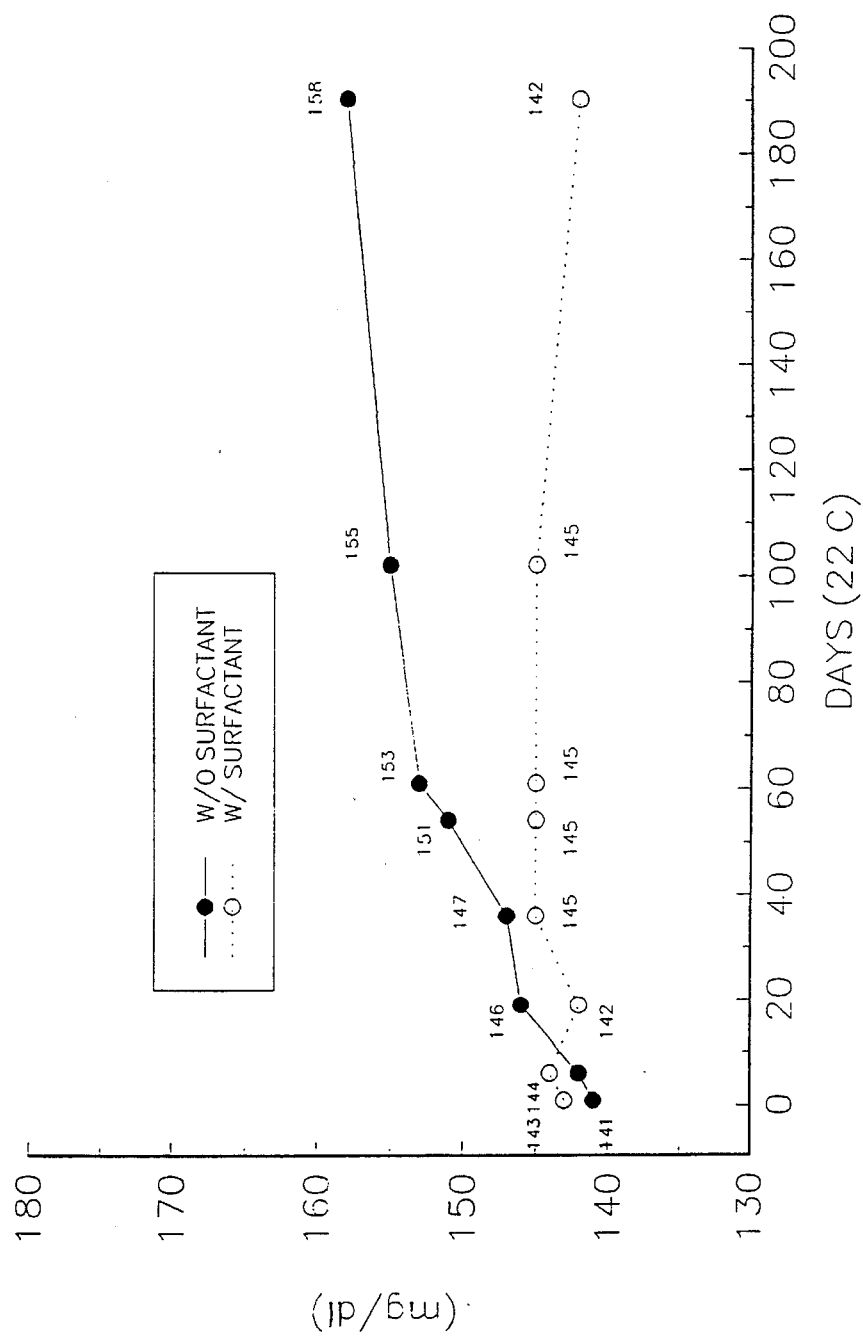
FIG. 1 is a graph illustrating triglyceride stability.

An accurate, stable, liquid, lipoprotein control composition is provided. The control composition of the present invention preferably comprises lipoprotein, surfactant and a divalent cation. The control may further comprise a chelating agent. In a preferred embodiment, the control composition comprises by weight from about 0.1% to about 1.5% lipoprotein, from about 0.01% to about 0.5% surfactant and from about 0.05% to about 1.0% divalent cation. Methods of making and using the controls described herein are also provided.

The lipoprotein control composition of the present invention performs like native lipoprotein in serum and, unlike native lipoprotein in serum, is stable. The lipoprotein control is not lyophilized or frozen and therefore does not require thawing or reconstitution. The control composition of the present invention is stable for up to about 5 months at room temperature (about 22° C.) and up to about 12 months refrigerated (about 2° C. to about 10° C.).

Although the control composition of the present invention is described with respect to use as a lipoprotein control, it will be appreciated that the control composition may be used in other applications such as in a complete chemistry control which contains other constituents. For example, analytes such as bilirubin, glucose, potassium, urea, creatinine, sodium, uric acid, ALT (alanine aminotransferase), GGT (γ-glutamyltransferase) may be included in the control composition.

A broad range of surfactants may be employed in the control of the present invention including anionic, ionic, non-ionic and zwitterionic surfactants. The following surfactants are most preferred: Triton X705 (Sigma), Silwet 7614 (Union Carbide), Diazopon SS 837 (GAF Chemicals Corp.), pluroinic F-68 (BASF), Polyethylene Glycol 20,000 (Union Carbide) and dioctyl sodium sulfosuccinate. Triton X705 is highly preferred. In addition, although it is believed that any cation may be employed in the control of the present invention, divalent cations are preferred and manganese ($Mn^{++}$), calcium ($Ca^{++}$) and magnesium ($Mg^{++}$) divalent cations are most preferred. $Mg^{++}$ is highly preferred.

As noted above, chelating agents may also be added to the control of the present invention. Preferred chelating agents include ethylenediaminetetracetic acid (EDTA), ethyleneglycol-bis-(β-aminoethyl ether) $N,N,N^1,N^1$-tetraacetic acid (EGTA) and sodium citrate. EDTA is most preferred in an amount of up to about 12 mmol.

It has been found that the amount of surfactant employed in the composition of the present invention is directly related to the amount of divalent cation employed. Surprisingly, the amount of divalent cation employed is inversely related to the amount of lipoprotein employed. It would be expected that more divalent cation would be required at a higher lipoprotein concentrations. Hence, when the concentration of lipoprotein is increased, the concentration of divalent cation is decreased and when the concentration of surfactant is increased, the amount of divalent cation is likewise increased. For example, when Triton X705 is increased from about 0.175% to about 0.350%, the optimum $Mg^{++}$ concentration increases from about 6 mM to about 25 mM.

Without wishing to be bound by theory, it is believed that the surfactant of the composition of the present invention acts as a stabilizer of the lipoprotein in solution and the divalent cation eliminates the matrix problems of currently available controls by properly suspending the lipoprotein in solution. That is, the surfactant stabilizes the lipoproteins and prevents the development of aggregation, and the divalent cation allows the lipoproteins to act like native lipoprotein in human serum, Le. the difference between the way the lipoprotein in the control and the lipoprotein in serum react to various manipulations such as precipitation, is the same. It is also believed that the chelating agent stabilizes the divalent cation and inhibits any oxidation of lipoprotein caused by cations such as $Fe^{++}$ which may be present in traces.

Because the lipoprotein of the control substance composition behaves substantially similar to native lipoprotein in serum, the control composition of the present invention may be used with any known method of lipoprotein measurement. For example, total cholesterol and triglyceride control concentrations may be measured by known techniques. The VLDL and LDL cholesterol may then be precipitated from the control with reagents such as heparin, dextran sulfate and magnesium ion and the HDL cholesterol may then be measured by photometric techniques. The LDL cholesterol may then be calculated by subtracting the measured HDL cholesterol concentration and the estimated VLDL cholesterol (approximated as one-fifth of the triglyceride concentration) from total cholesterol. The measured and calculated values of the various lipoprotein components may then be compared to the known values of the control composition, in order to objectively evaluate the accuracy and precision of the lipoprotein testing procedure.

It will be appreciated that as used herein the term "stable" generally refers to maintaining consistency and more particularly, maintaining consistent values for various parameters over a determined period of time. The term "accurate" as referred to herein means providing consistent results substantially similar to known values.

It will also be appreciated by those skilled in the art that the composition of the present invention may include other additives such as antimicrobial agents. It will further be understood that with the teachings of the present application, the skilled artisan will, and without undue experimentation, be enabled to alter concentrations of various components of the composition of the present invention to achieve a desired result.

The following Specific Examples will further describe the present invention.

SPECIFIC EXAMPLE 1

A. Prior Art

Concentrates were prepared from human plasma using dextran sulfate and $Mg^{++}$ as precipitating agents. The methods for preparing high density and low density lipoproteins have been described in Burstein, M., Advan. Lipid. Res. 11:67–108 (1973). The HDL concentrate had an HDL cholesterol of 550 mg/dl. The LDL concentrate had an LDL cholesterol of 950 mg/dl. For these studies, the lipoprotein concentrates were added to a HEPES buffered 0.5% NaCl, pH 7.4, containing 2% bovine serum albumin (BSA). The LDL and HDL concentrates were added to the buffered saline to give the various concentrations of LDL and HDL desired.

To measure cholesterol, an Abbott CCX or a Boehringer Mannheim Reflotron was employed. The LDL and VLDL cholesterol was precipitated and the HDL cholesterol was measured in the supernatant. Several methods of precipitation are known and the most common methods employ either phosphotungstic acid or dextran sulfate with $Mg^{++}$. Four different phosphotungstic acid reagents were obtained from Sigma, Baxter, Beckman, and DuPont. Each reagent is slightly different in composition. In addition, three different dextran sulfate reagents were obtained from Sigma, Abbott, and DMA.

When the various precipitating agents were compared using the lipoprotein preparation of HDL and LDL, very large differences in HDL cholesterol were obtained. The standard deviation for the six reagents was 15.8. The C.V. was 18. Values as low as 72 mg/dl and as high as 111 mg/dl were found. This is an illustration of the "matrix effect" observed with traditional lipoprotein preparations.

B. Control Composition

Figure 2:
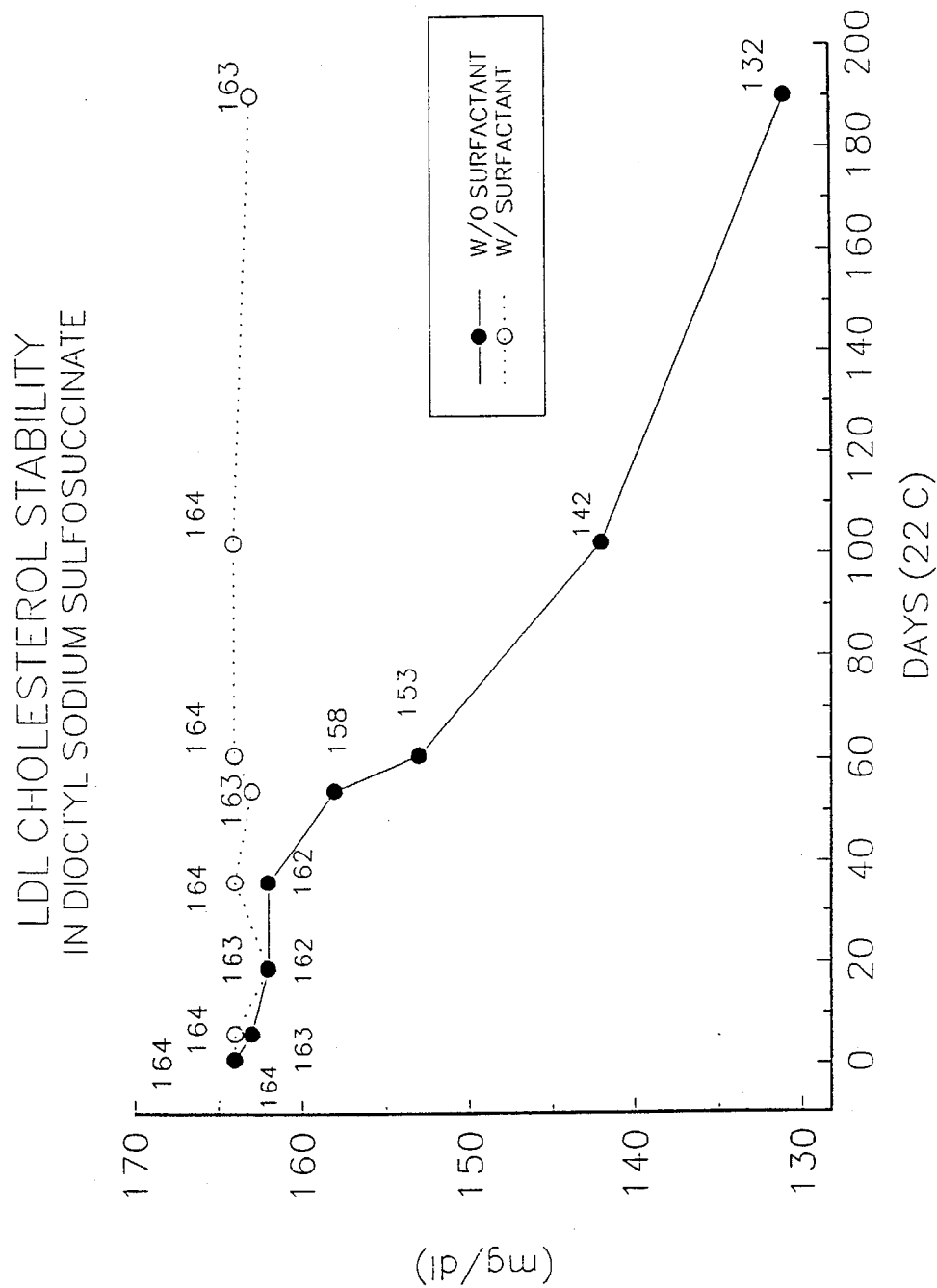
FIG. 2 is a graph illustrating LDL cholesterol stability.
Figure 3:
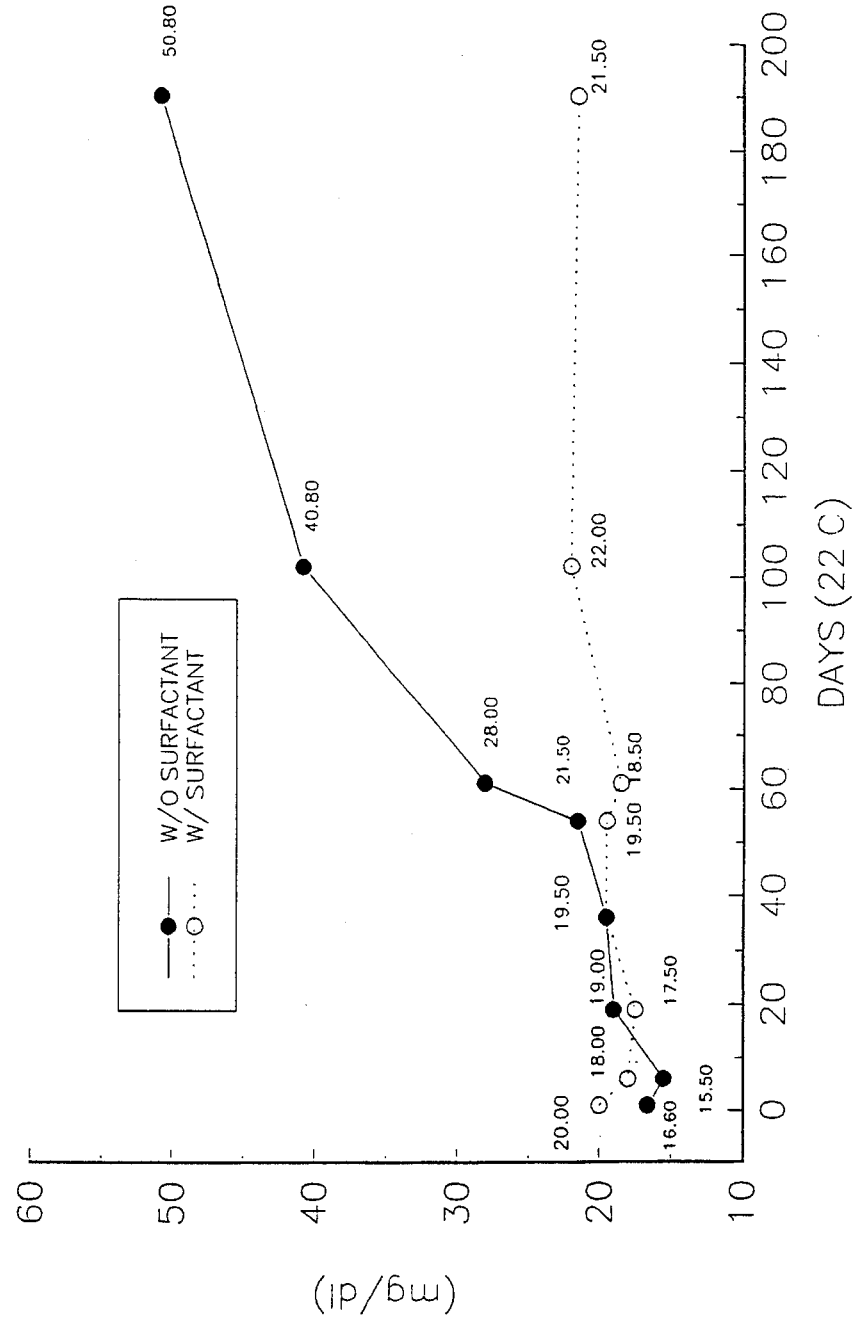
FIG. 3 is a graph illustrating HDL cholesterol stability.

A hypothesis was made that lipids tend to coalesce or aggregate in aqueous solutions. To keep them suspended, surfactants or wetting agents were added. The following surfactants were tested: Triton X705 (Sigma), Silwet 7614 (Union Carbide), Diazopon SS837 (GAF Chemicals Corp.), Pluronic F-68 (BASF), Polyethylene Glycol 20,000 (Union Carbide), and dioctyl sodium sulfosuccinate (Sigma). These surfactants were found to provide lipoprotein stability, Le.

the cholesterol levels were stable and the HDL and LDL cholesterol values were stable. The values are shown in FIGS. 1–3. The values set forth in FIGS. 1–3 were obtained using 150 mg/dl of dioctyl sodium sulfosuccinate. No significant change occurred over 200 days at 22° C. It is thus clear that a broad range of surfactants will stabilize the lipoprotein values for extended periods of time at room temperature.

The effect of varying the concentration of surfactant was examined by testing different concentrations of surfactant using the same concentration of lipoprotein. The results of this experiment is shown in Table 1 below. As shown in Table 1, as the concentration of Triton X705 is increased, the HDL cholesterol is increased. The higher concentrations of surfactant are thus inhibiting the precipitation of the LDL and VLDL and therefore the surfactants are stabilizing the lipoproteins. However, with surfactant alone, the lipoproteins do not behave in a manner similar to human serum and a severe matrix problem is produced as evidenced by the values in Table 1.

TABLE 1

Effect of Concentration of Surfactant

| Precipitating Reagent | Measured HDL Cholesterol mg/dl | | |
|---|---|---|---|
| | 0.05% X705 | 0.25% X705 | 0.50% X705 |
| Sigma (PTA) | 34.3 | 76.0 | 193 |
| Baxter (PTA) | 41.1 | 103 | 224 |
| Beckman (PTA) | 25.3 | 43.7 | 63.8 |
| DuPont (PTA) | 42.2 | 103 | 216 |
| Sigma (DEX) | 37.9 | 47.0 | 47.9 |
| Abbott (DEX) | 32.1 | 46.1 | 45.3 |
| DMA (DEX) | 35.8 | 47.1 | 44.5 |
| Mean: | 35.5 | 66.4 | 119 |
| S.D.: | 5.76 | 27.1 | 86.5 |
| C.V.: | 16.2% | 40.8% | 72.6% |

It was discovered that the addition of a divalent cation such as $Mg^{++}$, $Ca^{++}$, of $Mn^{++}$ will eliminate the matrix problems. In addition, it was discovered that the use of a chelating agent and in particular EDTA, stabilizes the divalent cation and also inhibits oxidation of the lipoprotein. (It is known that $Fe^{+++}$ ions in traces will cause oxidation of lipoproteins). The results of a study investigating the effect of divalent cation and EDTA are set forth in Table 2 below. In Table 2, Sample 1 is the control and thus contained no surfactant, no $MgCl_2$, and no EDTA. Sample 2 contained 0.175 g/dl Triton X705, no $MgCl_2$ and no EDTA. Sample 3 contained no Triton X705, 8 mM $MgCl_2$ and 3 mM EDTA. Sample 4 contained 0.175 g/dl Triton X705, 8 mM $MgCl_2$ and 3 mM EDTA.

TABLE 2

Effect of Surfactant (Triton X705) and a Divalent Cation ($MgCl_2$) on the Precipitation of LDL Values HDL Cholesterol mg/dl

| Precipitating Agent | Sample 1 | Sample 2 | Sample 3 | Sample 4 |
|---|---|---|---|---|
| Sigma (PTA) | 37.3 | 43.5 | 18.0 | 44.8 |
| DuPont (PTA) | 42.8 | 94.4 | 25.1 | 48.0 |
| Abbott (Dex) | 34.5 | 45.7 | 37.3 | 47.4 |
| Sigma (Dex) | 42.1 | 49.3 | 39.7 | 48.5 |
| Mean: | 39.2 | 58.2 | 30.0 | 47.2 |
| C.V.: | 10.2% | 41.6% | 34.3% | 3.53% |

The effect of varying the concentration of divalent cation was also investigated. Various concentrations of $MgCl_2$ were tested and the results are set forth in Tables 3 and 4 below. These data indicate that at 0.175 mg/dl of Triton X705, the optimum $Mg^{++}$ is approximately 6 mM. (Table 3: CV=5.6%) These data also indicate that as the concentration of lipoprotein is increased, the level of $Mg^{++}$ required decreased. This can be seen in Tables 3, 4A and 4B. As shown in Table 3, at the highest level of lipoprotein, the optimum $Mg^{++}$ concentration is 6 mM (HDLC cholesterol= 80 mg/dl). As shown in Table 4A, at the intermediate level of lipoprotein, wherein the HDL cholesterol concentration is 48 mg/dl, the optimum concentration is 8 mM $Mg^{++}$. As shown in Table 4B, at the lowest level of HDL cholesterol wherein the lipoprotein concentration is 24 mg/dl, the optimum concentration is 20 mM $Mg^{++}$.

TABLE 3

Effect of Divalent Cation Concentration
Values HDL Cholesterol mg/dl

| Precipitating Reagent | No Mg++ | MgCl at 6 mM | MgCl at 20 mM | MgCl at 30 mM |
|---|---|---|---|---|
| Sigma (PTA) | 94.3 | 74.6 | 40.4 | 49.7 |
| Baxter (PTA) | 106 | 80.6 | 47.1 | 40.4 |
| Beckman (PTA) | 72.9 | 74.5 | 68.7 | 17.1 |
| DuPont (PTA) | 111 | 82.9 | 53.6 | 44.2 |
| Sigma (DEX) | 75.1 | 82.0 | 80.5 | 79.0 |
| Abbott (DEX) | 76.3 | 82.0 | 84.2 | 83.3 |
| DMA (DEX) | 78.4 | 86.9 | 81.5 | 82.5 |
| Mean: | 87.6 | 80.5 | 65.1 | 56.6 |
| S.D.: | 15.8 | 4.50 | 18.0 | 25.5 |
| C.V.: | 18.0% | 5.60% | 27.7% | 45.2% |

TABLE 4A

Intermediate Lipoprotein Level
Values HDL Cholesterol mg/dl

| Precipitating Reagent | No Mg++ | MgCl at 8 mM | MgCl at 20 mM | MgCl at 30 mM |
|---|---|---|---|---|
| Sigma (PTA) | 76.0 | 44.9 | 34.8 | 32.4 |
| Baxter (PTA) | 103 | 47.6 | 34.7 | 30.2 |
| Beckman (PTA) | 43.6 | 43.9 | 40.8 | 38.7 |
| DuPont (PTA) | 103 | 48.9 | 35.9 | 29.6 |
| Sigma (DEX) | 47.0 | 50.0 | 44.9 | 41.4 |
| Abbott (DEX) | 46.1 | 47.5 | 47.5 | 45.5 |
| DMA (DEX) | 47.1 | 48.7 | 44.7 | 43.4 |
| Mean: | 66.4 | 47.4 | 40.5 | 37.3 |
| S.D.: | 27.1 | 2.21 | 5.38 | 6.53 |
| C.V.: | 40.8% | 4.70% | 13.3% | 17.5% |

TABLE 4B

Low Lipoprotein Level
Values HDL Cholesterol mg/dl

| Precipitating Reagent | No Mg++ | MgCl at 10 mM | MgCl at 20 mM | MgCl at 30 mM |
|---|---|---|---|---|
| Sigma (PTA) | 103 | 77.7 | 22.6 | 24.1 |
| Baxter (PTA) | 114 | 24.5 | 22.8 | 21.9 |
| Beckman (PTA) | 21.0 | 23.5 | 22.4 | 24.3 |
| DuPont (PTA) | 123 | 23.9 | 23.1 | 22.2 |
| Sigma (DEX) | 22.8 | 22.7 | 25.1 | 24.4 |
| Abbott (DEX) | 22.9 | 23.7 | 25.5 | 25.3 |
| DMA (DEX) | 24.3 | 23.4 | 24.9 | 24.7 |
| Mean: | 61.5 | 31.3 | 23.8 | 23.8 |
| S.D.: | 48.7 | 20.5 | 1.35 | 1.29 |
| C.V.: | 78.9% | 65.3% | 5.70% | 5.44% |

The effect of varying the concentration of chelating agent was also examined. In particular, various concentrations of EDTA were tested and the results are set forth in Table 5. It has been found that a higher concentration of surfactant requires more divalent cation. As the level of chelating agent is increased the $Mg^{++}$ is less available and the CV rises.

TABLE 5

Effect of Chelating Agent Concentration
Values HDL Cholesterol mg/dl

| Precipitation Reagent | No EDTA | 3 mM EDTA | 12 mM EDTA | 15 mM EDTA |
|---|---|---|---|---|
| Sigma | 39.0 mg/dl | 37.0 mg/dl | 33.2 mg/dl | 21.6 mg/dl |
| Baxter | 38.0 mg/dl | 37.8 mg/dl | 34.5 mg/dl | 23.4 mg/dl |
| Beckman | 39.0 mg/dl | 38.8 mg/dl | 36.9 mg/dl | 24.9 mg/dl |
| Abbott | 41.0 mg/dl | 40.2 mg/dl | 41.3 mg/dl | 40.8 mg/dl |
| Mean: | 39.3 mg/dl | 38.5 mg/dl | 36.5 mg/dl | 27.7 mg/dl |
| S.D.: | 1.3 | 1.4 | 3.6 | 8.9 |
| C.V.: | 3.2% | 3.6% | 9.8% | 32.0% |

When the concentration of surfactant is increased from the level shown as optimum, the lipoproteins are stable but do not precipitate as they should. Therefore, the HDL values are not correct and vary depending on the precipitating agent. However, it is possible to correct for the elevated surfactant by increasing the divalent cation concentration. To illustrate, Triton X705 was increased from 0.175% to 0.350% with the elevated level of lipoprotein (80 mg/dl). Table 6 below shows the results. Instead of the optimum $Mg^{++}$ concentration being 6 mM, the optimum is increased to 25 mM when the surfactant level is increased to 0.350%.

TABLE 6

Requirement for Increased Divalent Cation Concentration with an Increase in Surfactant Concentration
Values HDL Cholesterol mg/dl

| Precipitating Reagent | No Mg++ | Concentration $MgCl_2$ | | |
|---|---|---|---|---|
| | | 6 mM | 15 mM | 25 mM |
| Sigma (PTA) | 195 | 115 | 83.4 | 73.6 |
| Baxter (PTA) | 211 | 125 | 79.9 | 77.5 |
| Beckman (PTA) | 144 | 122 | 105 | 86.0 |
| Dupont (PTA) | 211 | 136 | 82.0 | 76.3 |
| Sigma (DEX) | 79.2 | 81.2 | 81.6 | 80.6 |
| Abbott (DEX) | 79.1 | 80.5 | 79.6 | 81.6 |
| DMA (DEX) | 79.5 | 80.2 | 81.6 | 76.9 |
| Mean: | 143 | 106 | 84.8 | 78.9 |
| S.D.: | 63.3 | 24.4 | 8.93 | 4.1 |
| C.V.: | 44.4% | 23.1% | 10.5% | 5.20% |

Materials and Methods

The following materials and methods were used in carrying out the experiments described herein.

Preparation of LDL cholesterol and triglyceride control. To 0.5 liter $H_2O$, add 11.91 g HEPES, 1.11 g EDTA, 0.1 g nalidixic acid, 0.3 g chloramphenicol, 0.4 g methylparaben, 5.0 g sodium chloride, 2.7 g Triton X705 and 20.0 g bovine serum albumin. Components stirred at 22° C. until dissolved. After addition of desired lipoprotein, volume is brought to 1.0 liter with $H_2O$.

| Component | Low Level | Intermediate Level | Elevated Level |
|---|---|---|---|
| [1] Avian Triglyceride Concentrate 4925 mg/dl | 11.5 ml | 16.0 ml | 36.0 ml |

-continued

| Component | Low Level | Intermediate Level | Elevated Level |
|---|---|---|---|
| [2] LDL Cholesterol Concentrate 950 mg/dl | 185 ml | 265 ml | 365 ml |

[1] Miles Pentex: Triglyceride Concentrate Triglycerides: 4925 mg/dl Cholesterol: 213 mg/dl
[2] LDL Cholesterol Concentrate LDL Cholesterol: 960 mg/dl HDL Cholesterol: <10 mg/dl Triglycerides: 390 mg/dl Preparation of LDL cholesterol, HDL cholesterol, and triglyceride control. To 0.5 liter $H_2O$, add 11.91 HEPES, 1.11 g EDTA, 0.1 g nalidixic acid, 0.3 g chloramphenicol, 0.4 g methylparaben, 5.0 g sodium chloride, 2.7 g Triton X705 and 20.0 g bovine serum albumin. Components stirred at 22° C. until dissolved. After addition of desired lipoprotein, volume is brought to 1.0 liter with $H_2O$.

| Component | Low Level | Intermediate Level | Elevated Level |
|---|---|---|---|
| $MgCl_2$ | 1.90 g | 0.76 g | 0.57 g |
| [1] Avian Triglyceride Concentrate 4925 mg/dl | 12.2 ml | 17.4 ml | 38.8 ml |
| [2] LDL Cholesterol Concentrate | 164 ml | 225 ml | 283 ml |
| [3] HDL Cholesterol Concentrate 550 mg/dl | 46.0 ml | 88.0 ml | 146 ml |

[1] Miles Pentex: Triglyceride Concentrate Triglycerides: 4925 mg/dl Cholesterol: 213 mg/dl
[2] LDL Cholesterol Concentrate LDL Cholesterol: 960 mg/dl HDL Cholesterol: <10 mg/dl Triglycerides: 390 mg/dl
[3] HDL Cholesterol Concentrate HDL Cholesterol: 550 mg/dl LDL Cholesterol: <10 mg/dl Triglycerides: 130 mg/dl Lipoprotein control prepared from human serum. To 1 liter human serum, add 1.11 g EDTA, 0.1 g nalidixic acid, 0.3 g chloramphenicol, 0.4 g methylparaben, $MgCl_2$ and 2.7 g Triton X705 to produced a 1 liter batch. Components stirred at 22° C. until dissolved. Levels may be adjusted by adding lipoprotein concentrate.

SPECIFIC EXAMPLE 2—STABILITY

Figure 4:
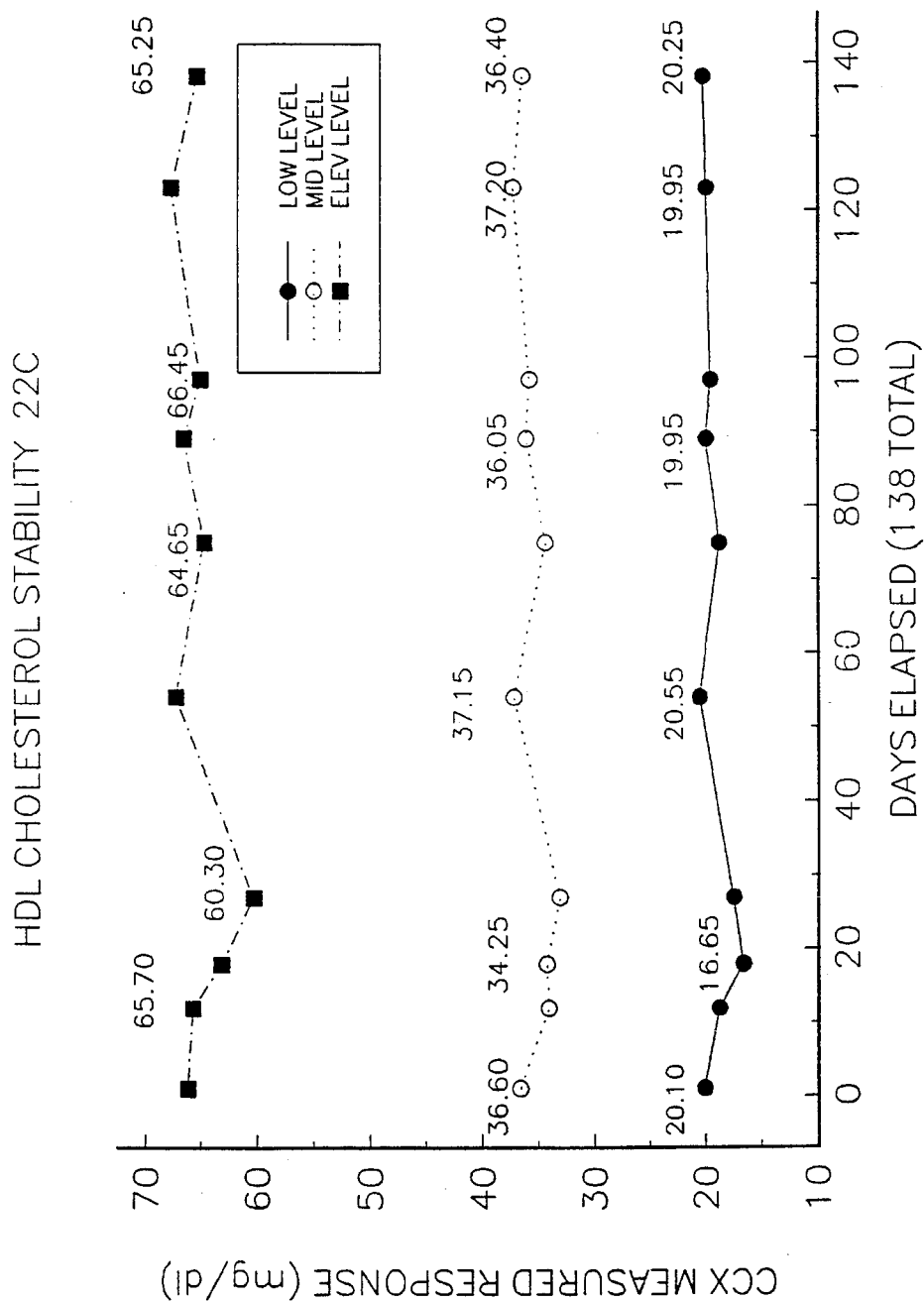
FIG. 4 is a graph illustrating HDL cholesterol stability at various concentration levels.
Figure 5:
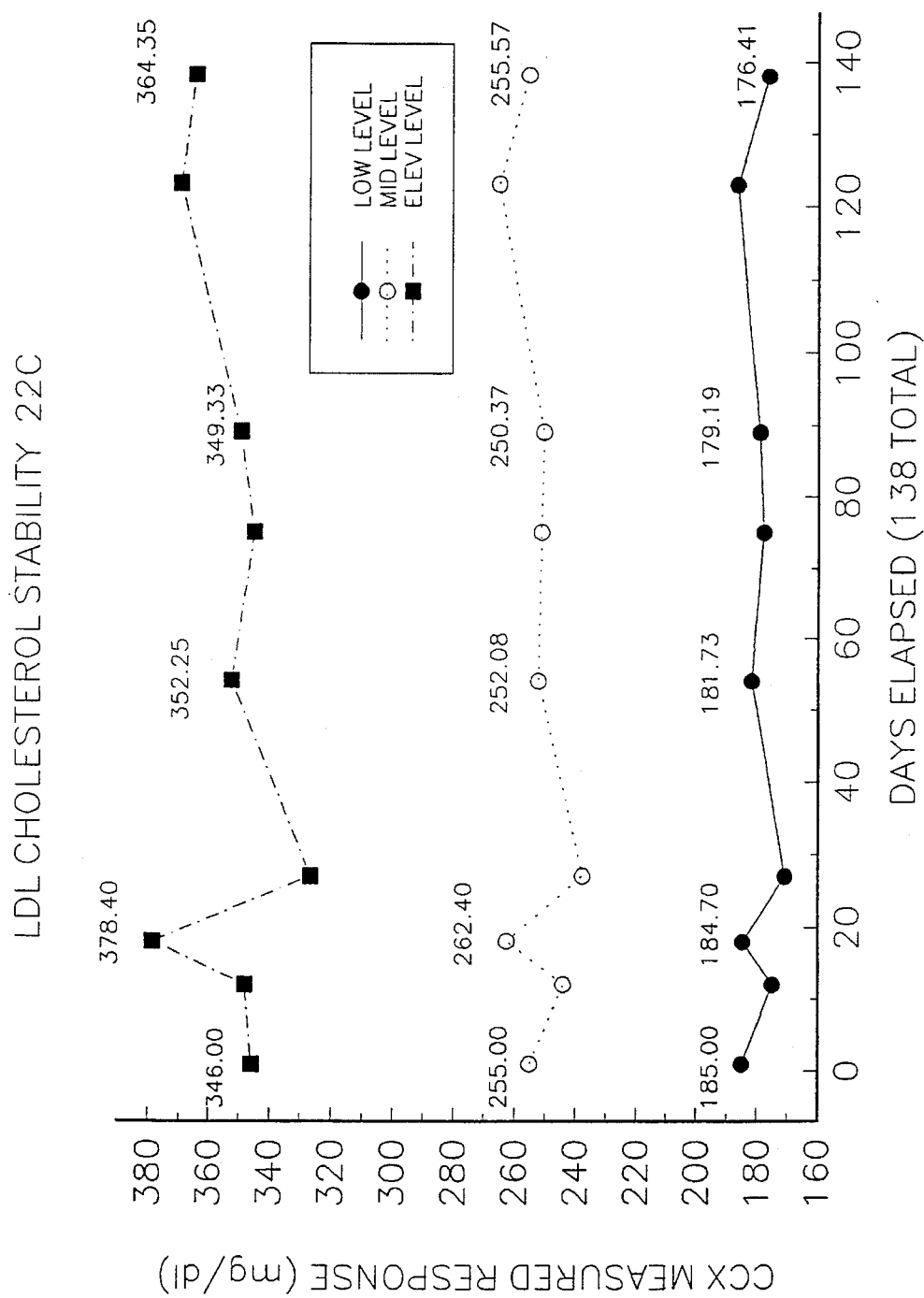
FIG. 5 is a graph illustrating LDL cholesterol stability at various concentration levels.
Figure 6:
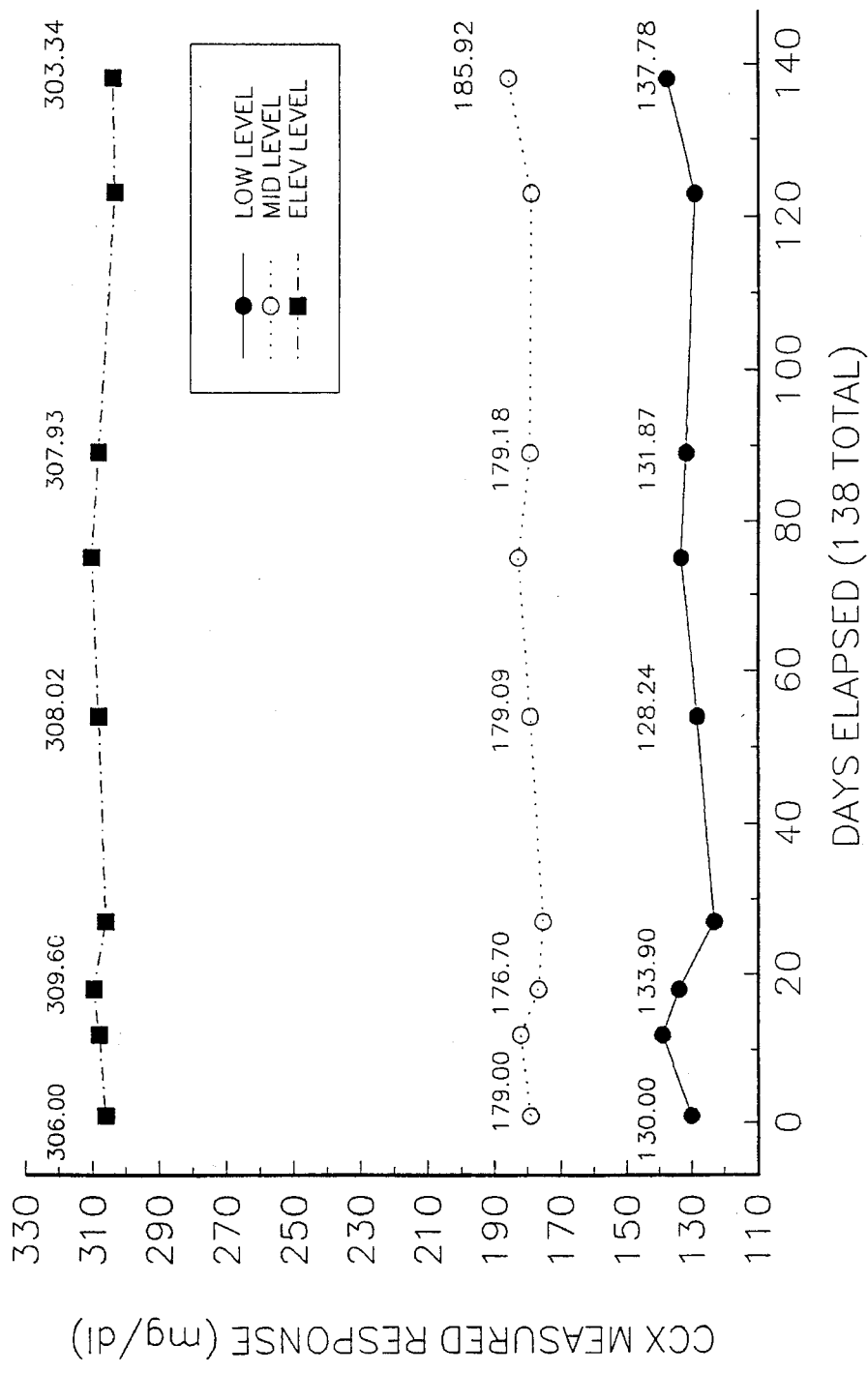
FIG. 6 is a graph illustrating triglyceride stability at various concentration levels.

Based on the above studies, using the appropriate concentration of lipoprotein, surfactant and divalent cation, liquid lipoprotein controls were prepared and their stability examined. It was found that the control composition of the present invention is stable for up to about 12 months at about 2° C. to about 10° C. and preferably at 6° C. (refrigeration temperature). Moreover, at about 22° C. (approximately room temperature), the control composition of the present invention is stable for up to about 5 months. FIGS. 4, 5 and 6 show the HDL cholesterol, LDL cholesterol and triglyceride stability, respectively, when low, mid and elevated levels of lipoprotein are present in the control. The control composition of the present invention may thus be stored as a liquid without hindering stability.

SPECIFIC EXAMPLE 3—MATRIX EFFECTS

As noted above, lyophilized and frozen lipid controls known in the art have matrix problems. In order to demonstrate this, a study was performed to compare various commercially-available controls with fresh human serum and the control of the present invention. The results of the study are set forth in Tables 7A–7E below. The data illustrates the matrix problems associated with the use of available commercial controls, in contrast to the results with human serum and the control of the present invention. In addition, three samples of human serum were tested with several precipitating agents. As shown, all the reagents perform equally well with human serum (see Table 7A). The C. V. between methods is 3%–4%. The control of the present invention gives a C. V. between methods that is close to normal serum (see Table 7B). The C. V. between methods using Sigma, CIBA-Corning, and Bio-Rad lipid controls illustrate the large matrix values in these prior art controls (see Tables 7C–7E).

TABLE 7A

Human Serum
Values HDL Cholesterol mg/dl

| Precipitating Reagent | Sample 1 | Sample 2 | Sample 3 |
|---|---|---|---|
| Sigma (PTA) | 22.2 | 43.7 | 57.8 |
| Baxter (PTA) | 22.0 | 46.1 | 58.5 |
| Beckman (PTA) | 23.0 | 42.2 | 58.1 |
| DuPont (PTA) | 23.1 | 44.9 | 63.0 |
| Sigma (DEX) | 24.6 | 45.1 | 61.9 |
| Abbott (DEX) | 24.3 | 42.2 | 58.3 |
| DMA (DEX) | 24.0 | 45.2 | 60.4 |
| Mean: | 23.3 | 44.2 | 59.7 |
| S.D.: | 1.03 | 1.55 | 2.10 |
| C.V.: | 4.42% | 3.52% | 3.51% |

TABLE 7B

Control of Invention
Values HDL Cholesterol mg/dl

| Precipitating Reagent | Level 1 | Level 2 | Level 3 |
|---|---|---|---|
| Sigma (PTA) | 22.6 | 44.9 | 75.6 |
| Baxter (PTA) | 22.8 | 47.6 | 80.6 |
| Beckman (PTA) | 22.4 | 43.9 | 74.5 |
| DuPont (PTA) | 23.1 | 48.9 | 82.9 |
| Sigma (DEX) | 25.1 | 50.0 | 82.0 |
| Abbott (DEX) | 25.5 | 47.5 | 82.0 |
| DMA (DEX) | 24.9 | 48.7 | 86.9 |
| Mean: | 23.8 | 47.4 | 80.5 |
| S.D.: | 1.35 | 2.21 | 4.50 |
| C.V.: | 5.70% | 4.70% | 5.59% |

TABLE 7C

Sigma Control*
Values HDL Cholesterol mg/dl

| Precipitating Reagent | Level 1 | Level 2 | Level 3 |
|---|---|---|---|
| Sigma (PTA) | 23.2 | 44.8 | 56.1 |
| Baxter (PTA) | 22.7 | 55.5 | 80.1 |
| Beckman (PTA) | 24.0 | 55.7 | 63.5 |
| DuPont (PTA) | 23.4 | 54.2 | 77.1 |
| Sigma (DEX) | 24.9 | 52.3 | 71.5 |
| Abbott (DEX) | 17.5 | 29.4 | 54.4 |
| DMA (DEX) | 27.4 | 42.8 | 66.7 |
| Mean: | 23.3 | 47.8 | 67.0 |
| S.D.: | 2.99 | 9.61 | 9.85 |
| C.V.: | 12.8% | 20.1% | 14.7% |

*Lyophilized

TABLE 7D

Ciba-Corning Control
Values HDL Cholesterol mg/dl

| Precipitating Reagent | Level 1 | Level 2 | Level 3 |
|---|---|---|---|
| Sigma (PTA) | 25.8 | 32.9 | 64.9 |
| Baxter (PTA) | 43.2 | 56.4 | 129 |
| Beckman (PTA) | 27.2 | 37.3 | 90.6 |
| DuPont (PTA) | 44.6 | 54.6 | 129 |
| Sigma (DEX) | 31.0 | 45.9 | 118 |
| Abbott (DEX) | 22.7 | 32.6 | 81.0 |
| DMA (DEX) | 25.3 | 38.3 | 92.4 |
| Mean: | 31.4 | 42.6 | 100 |
| S.D.: | 8.91 | 9.89 | 25.1 |
| C.V.: | 28.4% | 23.2% | 24.9% |

TABLE 7E

Bio-Rad Control
Values HDL Cholesterol Mg/dl

| Precipitating Reagent | Level 1 | Level 2 |
|---|---|---|
| Sigma (PTA) | 16.9 | 53.1 |
| Baxter (PTA) | 45.3 | 58.0 |
| Beckman (PTA) | 18.1 | 54.8 |
| DuPont (PTA) | 38.5 | 56.5 |
| Sigma (DEX) | 110 | 116 |
| Abbott (DEX) | 21.8 | 52.5 |
| DMA (DEX) | 58.8 | 58.3 |
| Mean: | 44.1 | 64.1 |
| S.D.: | 32.8 | 22.9 |
| C.V.: | 74.3% | 35.7% |

SPECIFIC EXAMPLE 4—PREFERRED PROCEDURE

The following is a detailed description of the preparation of a preferred control composition of the present invention.

A tri-level lipoprotein control is prepared containing clinically significant concentration levels for cholesterol, triglycerides and HDL cholesterol. Table 8 summarizes the constituent concentration of the control.

TABLE 8

| Measured Analytes | Level 1 | Level 2 | Level 3 |
|---|---|---|---|
| Cholesterol (mg/dl) | 150–200 | 230–280 | 330–380 |
| Triglycerides (mg/dl) | 120–150 | 170–200 | 290–350 |
| HDL Cholesterol (mg/dl) | 15.0–25.0 | 30.0–45.0 | 55.0–80.0 |

Stock Solution:

50 mM HEPES buffer with nalidixic acid (sodium salt at 10 mg %.

250 mM EDTA disodium in HEPES buffer, (93.06 g/l).

500 mM Magnesium Chloride ($MgCl_2$)in HEPES buffer, (47.62 g/l).

500 mM Nalidix Acid (sodium salt) in HEPES buffer, (5.00 g/l).

250 mM chloramphenicol in HEPES buffer, (2.50 g/l)

30.0% BSA, Protease Free 5.0% Sodium Chloride in HEPES buffer, (50.00 g/l).

10% Triton X705 in HEPES buffer.

Avian Triglyceride Concentrate (Miles).

Human LDL & HDL Cholesterol (Continental Services).

30% Triton X705 in HEPES buffer, (≈462.9 g/l).

It should be noted that the control is sensitive to microbial contamination and prolonged exposure to excessive heat (>30° C.). Any microbial contamination or prolonged exposure to high temperatures will compromise the stability of some components.

One liter of each level of control may be made using the stock solutions at the concentrations set forth in Table 9, combined in the order set forth in Table 9.

TABLE 9

Preferred Lipoprotein Control
Volumes of Stock Solution to Make 1 Liter of Control

| Stock Solution Lipid Control | Level 1 1 Liter | Level 2 1 Liter | Level 3 1 Liter |
|---|---|---|---|
| $MgCl_2$* | 40.0 ml | 16.0 ml | 12.0 ml |
| EDTA Disodium* | 12.0 ml | 12.0 ml | 12.0 ml |
| HEPES Buffer | 488 ml | 429 ml | 325 ml |
| Nalidixic Acid | 5.55 ml | 7.65 ml | 10.3 ml |
| Chloramphenicol | 86.6 ml | 74.2 ml | 58.1 ml |
| Triton X705 | 13.8 ml | 12.0 ml | 10.0 ml |
| Sodium Chloride | 75.4 ml | 67.0 ml | 57.0 ml |
| Avian Triglycerides | 2.00 ml | 2.50 ml | 20.0 ml |
| Albumin | 66.7 ml | 66.7 ml | 66.7 ml |
| Methylparaben | 0.288 g | 0.246 g | 0.185 g |
| LDL Cholesterol ≈950.0 mg/dl | 164 ml | 225 ml | 283 ml |
| HDL Cholesterol ≈550.0 mg/dl | 46.0 ml | 88.0 ml | 146 ml |

*Th $MgCl_2$ and EDTA Disodium are allowed to chelate for 10 minutes.

SPECIFIC EXAMPLE 5—MULTI-ANALYTE CONTROL

As described above, additional constituents such as analytes may be combined with the control composition of the present invention. Thus, a "multianalyte" or "complete chemistry" control is also within the scope of the present invention. The following is a list of tests which may be performed with a control composition of the present invention containing the appropriate constituents: potassium, BUN, glucose, uric acid, bilirubin, creatinine, sodium, alanine aminotransferase, γ-glutamyltransferase.

Table 10 indicates the various constituents and concentrations employed in a two level control to be used on chemistry analyzers (e.g. analogous to the Boehringer Refiotron, Abbott Vision and Kodak Ektachem).

TABLE 10

| Measured Analyte (Units) | Level 1 | Level 2 |
|---|---|---|
| Cholesterol (mg/dl) | 170–190 | 250–270 |
| HDL Cholesterol (mg/dl) | 45.0–52.0 | 20.0–27.0 |
| Triglycerides (mg/dl) | 170–200 | 280–320 |
| Bilirubin (mg/dl) | 1.10–1.40 | 4.60–5.20 |
| Creatinine (mg/dl) | 1.30–1.60 | 4.90–5.50 |
| Glucose (mg/dl) | 90.0–105 | 40.0–50.0 |
| Potassium (mmol/l) | 3.0–4.0 | 7.0–9.0 |
| Urea (mg/dl) | 27.0–33.0 | 47.0–55.0 |
| Uric Acid (mg/dl) | 6.00–7.00 | 8.00–9.00 |

Stock Solution:

50 mM HEPES buffer with Nalidix Acid (sodium salt) at 10 mg %.

225 mM EDTA Disodium in HEPES buffer, (83.75 g/l).

500 mM Magnesium Chloride ($MgCl_2$) in HEPES buffer, (47.60 g/l).

0.50% Nalidixic Acid (sodium salt) in $_dH_2O$, (5.00 g/l).

250 mg % Chloramphenicol in HEPES buffer, (2.50 g/l).

1M Potassium Chloride (KCL) in HEPES buffer, (74.55 g/l).

3% Urea (BUN) in HEPES buffer, (30.00 g/l).

0.5% ANS (Bilirubin) in HEPES buffer, (5.00 g/l).

20% Glucose in HEPES buffer, (200.00 g/l).

1.0% Uric Acid in HEPES buffer, (1.00 g/l).

30.0% BSA, Protease Free, (Hematology Grade).

5.0% Sodium Chloride in HEPES buffer, (50.00 g/l).

10% Triton X705 in HEPES buffer.

Avian Triglyceride Concentrate (Miles)

Human LDL and HDL Cholesterol. (Continental Services)

30% Triton X705 in HEPES buffer, (≈462.9 g/l).

One liter of each level of control may be made using the stock solutions as the concentrations set forth in Table 11, combined in the order set forth in Table 11.

TABLE 11

Multi-Analyte Control With Lipoproteins
Volumes of Stock Solution to Add to Make 1 Liter of Control

| Stock Solution Multi-Analyte | Level 1 1 Liter | Level 2 1 Liter |
|---|---|---|
| MgCl$_2$* | 30.0 ml | 30.0 ml |
| EDTA Disodium* | 12.0 ml | 12.0 ml |
| HEPES Buffer | 398 ml | 277 ml |
| Nalidixic Acid | 5.90 ml | 7.45 ml |
| Chloramphenicol | 84.5 ml | 75.3 ml |
| KCL (Potassium) | 4.50 ml | 7.00 ml |
| Urea (BUN) | 22.0 ml | 40.0 ml |
| ANS (Biulirubin) | 1.40 ml | 7.50 ml |
| Glucose | 5.00 ml | 2.50 ml |
| Creatinine | 1.20 ml | 5.60 ml |
| Uric Acid | 70.0 ml | 100 ml |
| Triton X705 | 13.6 ml | 12.4 ml |
| Sodium Chloride | 57.0 ml | 51.0 ml |
| Avian Triglycerides | 2.50 ml | 15.0 ml |
| Albumin | 66.7 ml | 66.7 ml |
| Methylparaben | 0.280 g | 0.250 g |
| LDL Cholesterol | 138 ml | 248 ml |
| HDL Cholesterol | 88.0 ml | 43.0 ml |

*The MgCl$_2$ and EDTA Disodium are allowed to chelate for 10 minutes.

Again it should be noted that the control is sensitive to microbial contamination and excessive heat. Any microbial contamination or prolonged exposure to high temperatures will compromise the stability of some components.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and references cited herein are incorporated by reference.

We claim:

1. A liquid lipoprotein control composition comprising:
   a) a lipoprotein;
   b) a surfactant present in an amount directly proportional to the amount of lipoprotein; and
   c) a divalent cation present in an amount inversely proportional to the amount of lipoprotein.

2. The composition of claim 1, wherein the lipoprotein is selected from the group consisting of HDL cholesterol, LDL cholesterol and triglyceride.

3. The composition of claim 1, wherein the divalent cation is selected from the group consisting of $Mg^{++}$, $Ca^{++}$ and $Mn^{++}$.

4. The composition of claim 1, wherein the lipoprotein comprises from about 0.1% to about 1.5% by weight of the composition, the surfactant comprises from about 0.01% to about 0.5% by weight of the composition, and the divalent cation comprises from about 0.05% to about 1.0% by weight of the composition.

5. The composition of claim 1, further comprising a chelating agent.

6. The composition of claim 1, further comprising a compound selected from the group consisting of glucose, bilirubin, potassium, urea, creatinine, sodium, uric acid, alanine aminotransferase and y-glutamyltransferase.

7. The composition of claim 5, wherein the chelating agent is selected from the group consisting of EDTA, EGTA and sodium citrate.

8. A method of determining the accuracy of a lipoprotein determination method comprising the steps of:
   a) providing a liquid lipoprotein control composition having a known lipoprotein concentration, wherein the composition comprises a lipoprotein, a surfactant present in an amount directly proportional to the amount of lipoprotein and a divalent cation present in an amount inversely proportional to the amount of lipoprotein;
   b) determining the lipoprotein concentration of the control composition; and
   c) comparing the concentration of lipoprotein obtained in step b) with the known lipoprotein concentration.

9. The method of claim 8, wherein the lipoprotein is selected from the group consisting of HDL cholesterol, LDL cholesterol and triglyceride.

10. The method of claim 8, wherein the divalent cation is selected from the group consisting of $Mg^{++}$, $Ca^{++}$ and $Mn^{++}$.

11. The method of claim 8, wherein the lipoprotein comprises from about 0.1% to about 1.5% by weight of the composition, the surfactant comprises from about 0.01% to about 0.5% by weight of the composition, and the divalent cation comprises from about 0.05% to about 1.0% by weight of the composition.

12. A liquid lipoprotein control composition comprising:
   a) HDL cholesterol;
   b) LDL cholesterol;
   c) a surfactant present in an amount directly proportional to the amount of HDL cholesterol and the amount of LDL cholesterol;
   d) a divalent cation present in an amount inversely proportional to the amount of HDL cholesterol and the amount of LDL cholesterol; and
   e) up to about 12 mmol chelating agent,
   wherein the control is stable for up to about six months at about 2° C. to about 10° C.

13. The control of claim 12, wherein the divalent cation is selected from the group consisting of $Mg^{++}$, $Ca^{++}$ and $Mn^{++}$.

14. The control of claim 12, wherein the chelating agent is selected from the group consisting of EDTA, EGTA and sodium citrate.

15. The control of claim 12, further comprising a compound selected from the group consisting of glucose, bilirubin, potassium, urea, creatinine, sodium, uric acid, alanine aminotransferase and y-glutamyltransferase.

* * * * *

UNITED STATES PATENT AND TRADEMARK OFFICE
CERTIFICATE OF CORRECTION

PATENT NO. : 5,614,414  Page 1 of 2
DATED : March 25, 1997
INVENTOR(S) : Wayne L. Ryan et al.

It is certified that error appears in the above-identified patent and that said Letters Patent is hereby corrected as shown below:

Column 1, line 45, delete "."

Column 4, line 8, "y-glutamyltransferase" should be --γ-glutamyltransferase--.

Column 4, line 50, "L.e." should be --i.e.--.

Column 5, line 42, "Mannhelm" should be --Mannheim--.

Column 5, line 67, "L.e." should be --i.e.--.

Column 8, line 45, "4.1" should be --4.11--.

Column 10, line 15, "C1BA" should be --CIBA--.

Column 12, line 43, "y-glutamyltransferase" should be --γ-glutamyltransferase--.

Column 12, line 47, "Refiotron" should be --Reflotron--.

UNITED STATES PATENT AND TRADEMARK OFFICE
CERTIFICATE OF CORRECTION

PATENT NO. : 5,614,414
DATED : March 25, 1997
INVENTOR(S) : White, III et al.

It is certified that error appears in the above-identified patent and that said Letters Patent is hereby corrected as shown below:

Column 14, line 15, Claim 6, "y-glutamyltransferase" should be --$\gamma$-glutamyltransferase--.

Column 14, lines 31, 32, Claim 8, "after "b)" no new paragraph.

Column 14, line 65, Claim 15, "y-glutamyltransferase" should be --$\gamma$-glutamyltransferase--.

Signed and Sealed this

Twenty-fifth Day of August, 1998

Attest:

BRUCE LEHMAN

Attesting Officer

Commissioner of Patents and Trademarks